United States Patent [19]
Eibofner

[11] Patent Number: 4,975,056
[45] Date of Patent: Dec. 4, 1990

[54] MEDICAL, ESPECIALLY DENTAL HANDPIECE

[75] Inventor: Eugen Eibofner, Biberach, Fed. Rep. of Germany

[73] Assignee: Kaltenbach & Voigt GmbH & Co., Biberach an der Riss, Fed. Rep. of Germany

[21] Appl. No.: 378,844

[22] Filed: Jul. 12, 1989

[30] Foreign Application Priority Data

Aug. 25, 1988 [DE] Fed. Rep. of Germany ....... 3828866

[51] Int. Cl.⁵ .............................................. A61C 3/02
[52] U.S. Cl. ...................................... 433/84; 433/165; 433/115
[58] Field of Search .................. 433/84, 165, 166, 115, 433/127

[56] References Cited

U.S. PATENT DOCUMENTS

| | | | |
|---|---|---|---|
| 2,098,317 | 11/1937 | Stauut | 433/115 |
| 3,762,052 | 10/1973 | Melde | 433/165 |
| 4,369,034 | 1/1983 | Garuier et al. | 433/115 |

FOREIGN PATENT DOCUMENTS

| | | | |
|---|---|---|---|
| 181358 | 3/1955 | Fed. Rep. of Germany | 433/115 |
| 1002502 | 2/1957 | Fed. Rep. of Germany | 433/165 |
| 1018583 | 10/1957 | Fed. Rep. of Germany | 433/128 |
| 3433570 | 3/1986 | Fed. Rep. of Germany | . |

Primary Examiner—John Weiss
Attorney, Agent, or Firm—Scully, Scott, Murphy & Presser

[57] ABSTRACT

A medical handpiece, and especially a dental handpiece, including a drivable worktool or implement which is rotatably supported with its shaft at one end of the handpiece and which projects from this handpiece end with its operating end. The implement possesses an elongate blind bore-like passageway which communicates with the outside at the work end of the implement through the intermediary of a discharge opening, and with which there is associated a supply line arranged within the handpiece for the infeed of cooling media to at least one radial through-opening of the implement which stands in communication with the elongate passageway; whereby the at least one radial through-opening is sealed with respect to the interior of the handpiece through the intermediary of a seal which encompassing the shaft of the implement and contacts against a wall portion of the handpiece.

20 Claims, 2 Drawing Sheets

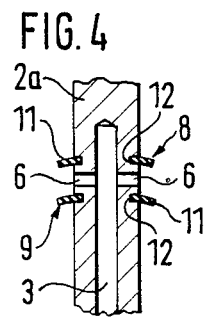
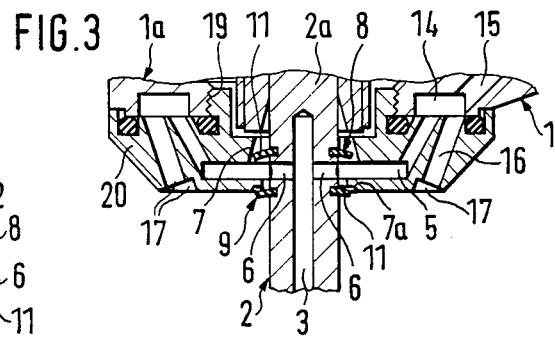
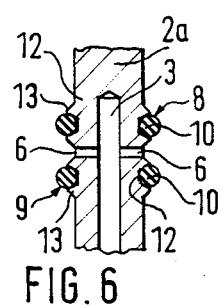
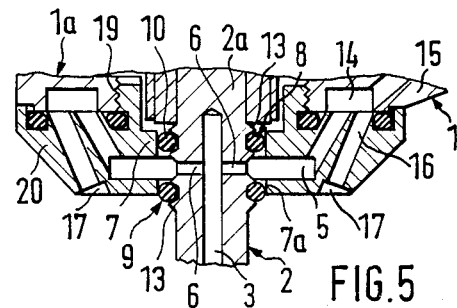
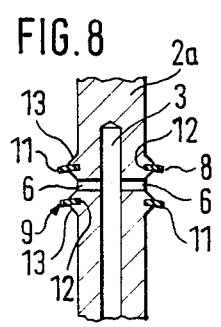
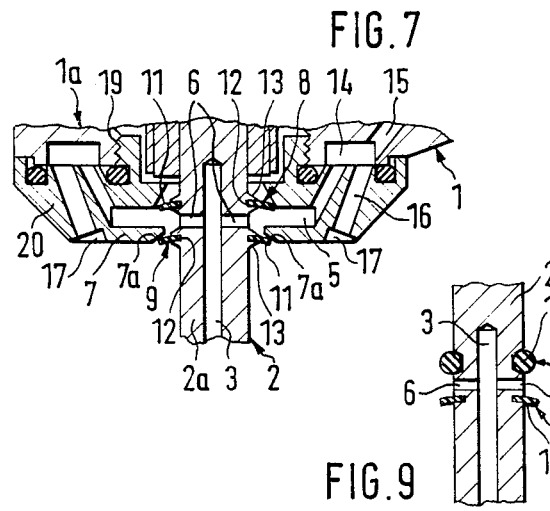
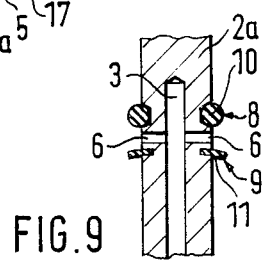

MEDICAL, ESPECIALLY DENTAL HANDPIECE

BACKGROUND OF THE INVENTION

1. Field of the Invention

The present invention relates to a medical handpiece, and especially a dental handpiece, including a drivable worktool or implement which is rotatably supported with its shaft at one end of the handpiece and which projects from this handpiece end with its operating end. The implement possesses an elongate blind bore-like passageway which communicates with the outside at the work end of the implement through the intermediary of a discharge opening, and with which there is associated a supply line arranged within the handpiece for the infeed of cooling media to at least one radial through-opening of the implement which stands in communication with the elongate passageway; whereby the at least one radial through-opening is sealed with respect to the interior of the handpiece through the intermediary of a seal which encompassing the shaft of the implement and contacts against a wall portion of the handpiece.

2. Discussion of the Prior Art

A dental handpiece of this type has already become known from the disclosure of German Pat. No. 34 33 570. In this known handpiece, the sealing device which is constructed in the form of a sealing ring encompasses the implement shaft in an axially movable manner such that, during the movement of the implement out of the handpiece; for instance; for the purpose of exchanging the implement, the sealing ring which axially contacts from above against the wall portion of the handpiece, remains within the handpiece so as to practically form a fixed component of the handpiece. As a consequence thereof, during the cleaning or respectively the sterilizing of the handpiece, because of the implement receiving opening of the handpiece being exposed or open as a result of the withdrawal of the implement, the relatively aggressive cleaning or sterilizing fluid penetrates into the handpiece and attacks the sealing ring, as a result of which the last-mentioned becomes brittle or flawed through this influence thereon and loses its sealing effect. Hereby, in that the sealing ring remains positioned within the handpiece in this known handpiece construction, it is not possible to exchange the sealing ring without any disassembling of the handpiece.

SUMMARY OF THE INVENTION

The present invention as described in more extensive detail hereinbelow obviates the disadvantages encountered in the prior art by providing a handpiece of the above-mentioned type wherein, especially when the sealing device is formed by a sealing ring, the latter is axially immovably arranged on the shaft of the implement which is inserted into the handpiece such that the sealing device and implement are commonly removable from the handpiece and commonly movable into the handpiece, and to thereby preclude any attack on the sealing device caused by cleaning or sterilizing liquid penetrating into the handpiece at a withdrawn implement, and thereby avoiding the resultant loss in the sealing effect of the seal.

The advantages which are achieved by the invention there can be essentially ascertained in that through the now possible common or joint withdrawal of the sealing device and implement from the handpiece, this precludes an attack on the seal during the cleaning or disinfecting of the handpiece. In the disassembled or withdrawn condition, a sealing device which forms a wear component, preferably a sealing ring, can be easily be pulled out of the workpiece and exchanged possibly with the assistance of tweezers or pliers.

BRIEF DESCRIPTION OF THE DRAWINGS

Reference may now be had to the following detailed description of exemplary embodiments of the handpiece pursuant to the invention, taken in conjunction with the accompanying drawings; in which:

FIG. 3 illustrates the end of the handpiece receiving the implement with seals formed from two sealing rings each having a cross-section in the shape of a flat strip;

FIG. 4 illustrates a fragmentary segment of the implement mounting the sealing rings of FIG. 3 in the condition withdrawn from the handpiece;

FIG. 5 illustrates the end of the handpiece receiving the implement mounting two sealing rings each having a cross-section in the shape of a circle;

FIG. 6 illustrates the portion of the implement mounting the sealing rings pursuant to FIG. 5 in the condition thereof withdrawn from the handpiece;

FIG. 7 illustrates a modified embodiment with respect to that shown in FIG. 3;

FIG. 8 illustrates the portion of the implement mounting the sealing rings of FIG. 7 in the condition thereof withdrawn from the handpiece; and FIG. 9 illustrates an embodiment which is modified with respect to those shown in FIGS. 4, 6 and 8.

DETAILED DESCRIPTION

Figures 1, 2:
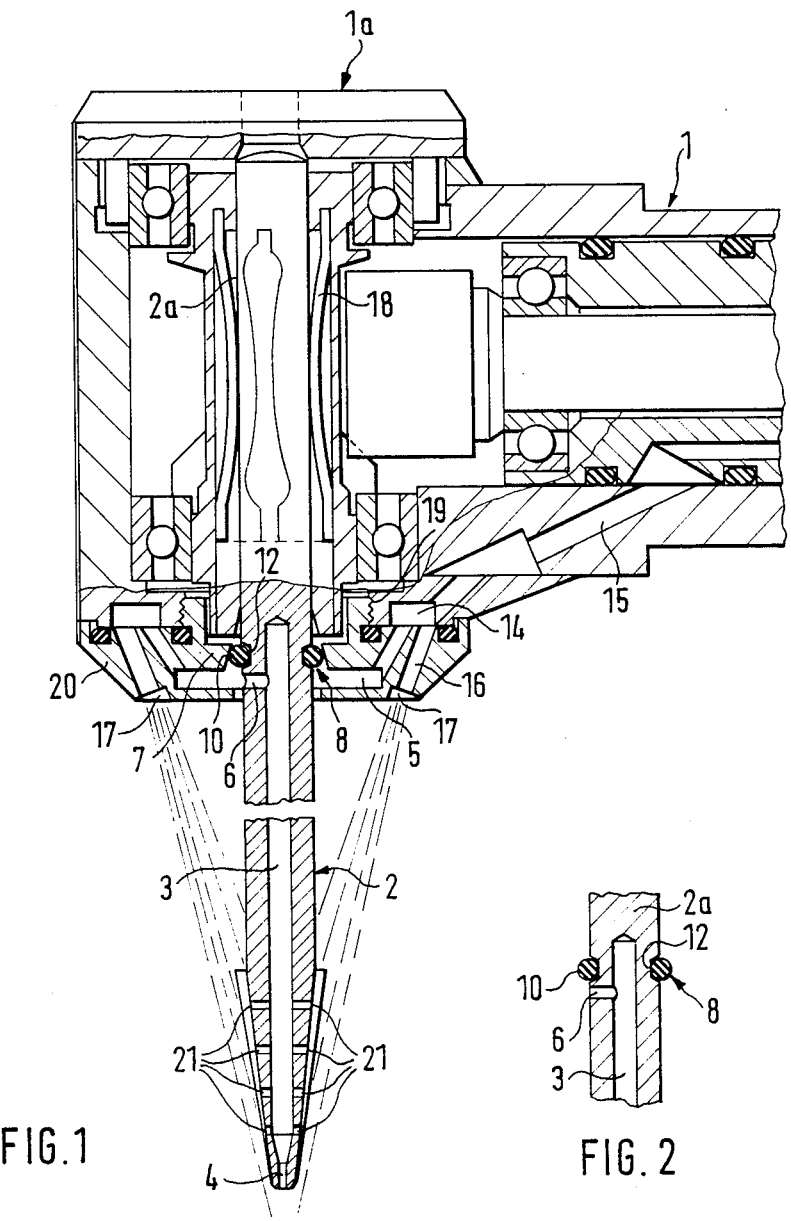
FIG. 1 illustrates a sectional view through the end of a handpiece which receives an implement with a sealing ring forming a seal possessing a cross-section in the shape of a circle.
FIG. 2 illustrates a fragmentary segment of the portion of the implement mounting the sealing ring of FIG. 1; shown in the condition withdrawn from the handpiece.

The illustrated medical handpiece 1 can be medicinal in nature, for example a surgical handpiece, and especially in the form of a dental handpiece. The handpiece 1 can be constructed as a straight or an angled handpiece (not shown) or, as illustrated, as an angled handpiece. The elbow member. The head end of the elbow handpiece is identified by reference 1a. The handpiece 1, at one end thereof, possesses a drivable implement 2 which is rotatably supported on the handpiece with its shaft 2a, and which protrudes from this end of the handpiece. The implement 2 is constructed unitarily and incorporates an elongate blind bore-shaped passageway which communicates with the outside at the work end of the implement 2 by means of a discharge opening 4. Associated with the elongate passageway 3 is a supply conduit or line 5 which is arranged in the handpiece 1 for the supplying of cooling media; for example, such as water, to at least one radial opening 6 of the implement 2 which is in communication with the elongate passageway 3. The at least one radial opening 6 is sealed with regard to the interior of the handpiece; in essence, in the illustrated embodiment, with respect to the interior of the head 1a of the elbow piece through the intermediary of a seal element 8 which encompasses the implement shaft 2a and which contacts against a wall portion 7 of the handpiece 1.

The seal element 8 is axially immovably mounted in such a manner on the shaft 2a of the implement 2 which is inserted into the handpiece 1, such that the seal element 8 and the implement 2 can be jointly or commonly withdrawn from the handpiece 1, and are also commonly movable into the handpiece 1.

In this arrangement, of only a single seal element 8 (FIGS. 1 and 2), it is possible to provide a flow of cooling medium along the outer wall surface of the implement 2 in a direction towards the work end of the implement 2 which possesses the discharge opening 4. In order to also be able to interrupt such a kind of external flow of cooling medium, pursuant to FIGS. 2 through 9, at an axial distance from the above-mentioned seal element 8, on the other side of the at least one opening 6 when faces towards the work end of the implement 2, a still further seal element 9 is again immovably arranged on the implement shaft 2a such that this further seal element 9 together with the seal element 8 and the implement 2 can also be jointly withdrawn from the handpiece 1, and are also jointly movable into the handpiece 1. In this manner, there can be attained for the further seal element 9 the same advantages as regards the first-mentioned seal element 8.

In a desired instance, in a manner not illustrated herein, there can be also arranged a larger number of seal, for example, three or four seal elements, on the implement shaft 2a.

As may be readily ascertained in FIG. 1 for the one seal element 8, and in FIGS. 3 and 7 for presently the upper seal element 8, the wall portion 7 of the handpiece 1 which serves as the contact surface for the seal element or seal elements, is configured as a kind of an upwardly reducing cone, against which the respective seal contacts from below.

In particular, as may be ascertained from FIGS. 3, 5 and 7, the further seal element 9 contacts the sleeve wall structure 7a of the handpiece 1 axially from below (FIG. 3) and/or radially sideways (FIGS. 5 and 7).

As is shown from the drawing, the seal element 8, or respectively the seal elements 8 and 9, are each formed by a sealing ring.

The sealing ring or the sealing rings 8 and respectively 9, can each possess a cross-section in the shape of a circle 10, or a cross-section which is in the shape of a flat, essentially radially outwardly protruding strip member 11.

As can be especially derived from a comparison between FIGS. 3 and 4, as well as FIG. 7 and 8, the sealing rings 8 and respectively 9, which each have a cross-section in the shape of a flat strip member 11, are constructed in such a manner that, during the standstill or inoperative condition of the implement 9, extending from the interior outwardly they are slightly inclined downwardly towards the bottom towards the work end of the implement, and during rotation of the implement, as a consequence of centrifugal force, press upwardly into the sealing position in contact against the wall portion 7, and respectively 7a, of the handpiece 1.

In the embodiment pursuant to FIG. 9, a sealing ring 8 is arranged on the one side of the at least one radial opening 6; in essence at the upper side, which ring has a cross-section in the shape of a circle 10; whereas on the other side; in effect, the lower side of the opening 6, there is arranged a sealing ring 9 having a cross-section in the shape of a flat strip member 11.

The sealing rings 8, 9 can be basically mounted with a friction fit on the implement shaft 2a. In that regard, it is expedient, as is illustrated, that the sealing ring or the seal rings 8 and respectively 9, are mounted with a close fit on the implement shaft 2a. For this purpose, the sealing rings 8, 9 are respectively arranged in an annular groove 12 formed in the implement shaft 2a. In order that the implement shaft 2a is not imparted any weakening in its structure through the provision of the annular groove 12, in the embodiments pursuant to FIGS. 5 through 8, each annular groove 12 presently provided in an annular bead 13 formed on the implement shaft 2a.

In the embodiment pursuant to FIGS. 1 and 2 there is provided a radial opening 6, whereas in the embodiments pursuant to FIG. 3 through 9 there are provided two expediently diametrically oppositely-located openings 6.

As is illustrated in FIGS. 1, 3, 5 and 7, the construction relative to the supply of cooling medium to the implement 2 is such that the cooling medium inlet conduit 5, which is associated with the elongate passageway 3 in the implement 2, extends from an annular collector passageway 14 arranged in the handpiece 1 and which is in communication with a supply passageway 15 for cooling medium. Hereby, provided are a plurality; for example, two cooling medium supply conduits 5. However, also three supply conduits 5 for cooling medium can be arranged spaced about the circumference of the head of the elbow piece. Instead thereof, the supply conduit 5 for cooling medium can also be constructed as an annular passageway. As is ascertainable from FIGS. 1, 3, 5 and 7, branching off from the annular collector passageway 14 are conduits 16 leading to nozzles 17 which are directed against the work end of the implement 2. Also in this case can there be provided three conduits 16 with nozzles 17 which are spaced about the circumference of the head of the elbow piece.

As is illustrated in FIG. 1, the implement 2 is retained in the handpiece 1 by means of a clamping element 18 so as to be releasable; for example, withdrawable from the handpiece 1. The clamping element 18 is hereby formed as an ordinary clamping jaw.

As is shown in FIGS. 1, 3, 5 and 7, the head 1a of the elbow piece includes a cover 20 which can be screwed together with the head 1a by means of screwthreads 19, and which contains the supply conduits 5 and the conduits 16 with the nozzles 15. As desired, the cover 20 can be unscrewed, and exchanged with a cover which does not include conduits 16 or nozzles 15; however, with supply conduits 5.

The implement 2, in accordance with FIG. 3, in addition to the above-mentioned elongate passageway discharge opening 4, which is axially directed, can also be provided with radial discharge openings 21 extending from the elongate passageway 3.

What is claimed is:

1. Medical handpiece, especially a dental handpiece including a drivable implement having a shaft for being rotatably supported at one end of said handpiece; said shaft protruding from said end, said implement having an elongate blind bore-shaped passageway communicating with the exterior at a work end of the implement through a discharge opening; said implement including at least a radial opening in communication with said elongate passageway and which connects with a supply conduit in the handpiece for the infeed of a cooling medium, said at least one radial opening being sealed relative to the interior of the handpiece by seal means contacting a wall portion of the handpiece, and said seal means encompassing the implement shaft, said seal means being axially immovably mounted on the shaft of the inserted implement such that the seal means and the implement are commonly withdrawable from the handpiece and commonly insertable into the handpiece.

2. Handpiece as claimed in claim 1, wherein a second seal means is axially immovably mounted on said shaft at an axial distance from the first-mentioned seal means on the other side of said at least one radial opening facing towards the work end of the implement, and said further seal means and said implement are commonly withdrawable from the handpiece and insertable into the handpiece.

3. Handpiece as claimed in claim 2, wherein the wall portion against which the seal means contact is configured as an upwardly reducing cone against which the at least one seal means contacts from below thereof.

4. Handpiece as claimed in claim 2, wherein said further seal means contacts axially from below against a sleeve wall structure of the handpiece.

5. Handpiece as claimed in claim 2, wherein said further seal means contacts radially sideways against a sleeve wall structure of the handpiece.

6. Handpiece as claimed in claim 2, wherein said seal means are constituted from seal rings.

7. Handpiece as claimed in claim 6, wherein at least one said seal ring has a circular cross-section.

8. Handpiece as claimed in claim 6, wherein said seal rings have a cross-section in the shape of a flat strip which extends substantially radially.

9. Handpiece as claimed in claim 8, wherein said seal rings having as cross-section in the shape of flat strip are configured that during the standstill of the implement there are slightly inclined downwardly towards the work end of the implement and during rotation of the implement press upwardly in response to centrifugal force into a sealing position in contact with a wall portion of the handpiece.

10. Handpiece as claimed in claim 7, wherein on one side of said at least one radial opening there is arranged a first seal ring having a circular cross-section and on the other side of said opening there is mounted a seal ring having a cross-section in the shape of a flat strip.

11. Handpiece as claimed in claim 6, wherein said seal rings are mounted in annular grooves on the implement shaft.

12. Handpiece as claimed in claim 11, wherein each annular groove is formed in an annular bead on the implement shaft.

13. Handpiece as claimed in claim 1, including two openings which are sealed by said seal means.

14. Handpiece as claimed in claim 13, wherein the two openings are located diametrically opposite each other.

15. Handpiece as claimed in claim 1, wherein the cooling medium supply conduit which is associated with the elongate passageways in the implement extends from an annular collector passageway communicating with a cooling medium supply passageway.

16. Handpiece as claimed in claim 15, including a plurality of said cooling medium supply conduits.

17. Handpiece as claimed in claim 1, wherein the cooling medium supply conduit is an annular passageway.

18. Handpiece as claimed in claim 15, wherein conduits branch off from said annular collector passageway include nozzles which are directed against the work end of the implement.

19. Handpiece as claimed in claim 1, wherein the implement is detachably retained in the handpiece by a clamping element.

20. Handpiece as claimed in claim 19, wherein the clamping element is formed from clamping jaws.

* * * * *